United States Patent [19]

Shillington et al.

[11] Patent Number: 4,600,112

[45] Date of Patent: Jul. 15, 1986

[54] ONE-WAY PASS-THROUGH CLOSURE

[75] Inventors: Richard A. Shillington, San Clemente; Alec Oberschmidt, Leucadia, both of Calif.

[73] Assignee: Med-Safe Systems, Inc., Encinitas, Calif.

[21] Appl. No.: 672,630

[22] Filed: Nov. 19, 1984

[51] Int. Cl.⁴ .............................................. A61M 5/32
[52] U.S. Cl. .................................... 215/274; 215/307; 215/306; 206/366; 220/229
[58] Field of Search ...................... 215/307, 274, 306; 206/366, 365; 220/229

[56] References Cited

U.S. PATENT DOCUMENTS

| | | | |
|---|---|---|---|
| 3,899,100 | 8/1975 | Rigaud | 220/229 |
| 4,454,944 | 6/1984 | Shillington et al. | 206/366 |
| 4,494,652 | 1/1985 | Nelson | 206/366 |
| 4,520,926 | 6/1985 | Nelson | 206/366 |

Primary Examiner—Donald F. Norton
Attorney, Agent, or Firm—Baker, Maxham & Jester

[57] ABSTRACT

A pass-through closure for disposable receptacles includes a rim for mounting the walls surrounding an opening in a receptacle and a plurality of generally triangular shaped flaps extending inwardly and axially to form a closure having a generally conical configuration enabling passage of articles through the closure in one direction.

8 Claims, 4 Drawing Figures

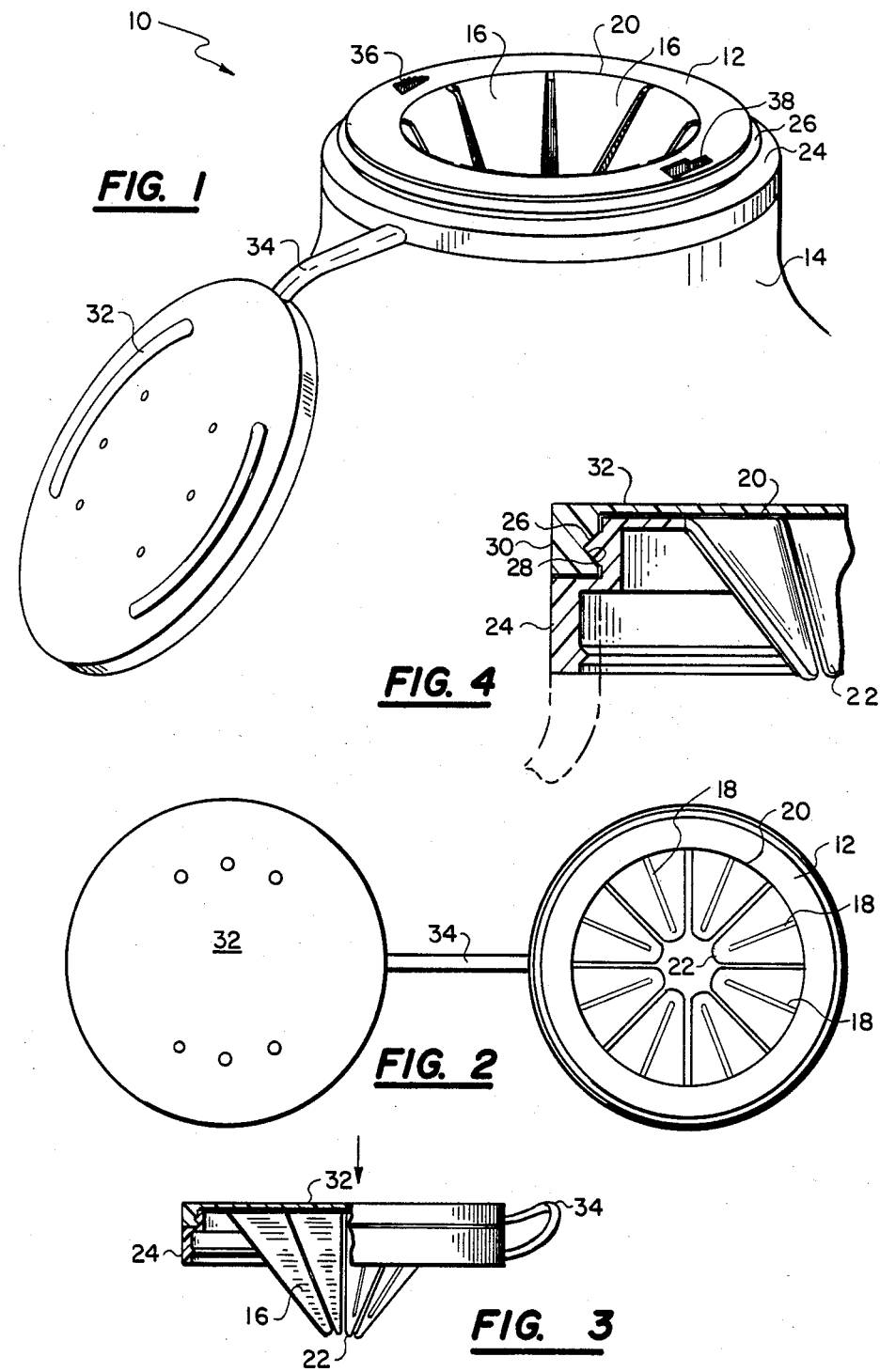

ONE-WAY PASS-THROUGH CLOSURE

BACKGROUND OF THE INVENTION

The present invention relates to closures and pertains particularly to one-way pass-through closures for disposable receptacles.

In our U.S. Pat. No. 4,454,944 entitled "One-Way Sharps Receptacle", issued June 19, 1984, we disclose a disposable receptacle for disposing of sharp, hazardous objects such as syringes and the like. In the aforementioned patent, a pass-through closure is disclosed wherein the closure is normally closed but permits an object or article to be passed through the closure, generally in one direction such that once started, the article must be continued in that direction. The closure is also designed to inhibit the insertion and withdrawal of a hand to retrieve an article from a container.

While the aforementioned closure is effective to discourage the removal of articles from a container, it is desirable that improved pass-through closures be available.

SUMMARY AND OBJECT OF THE INVENTION

It is the primary object of the present invention to provide an improved pass-through closure for containers In accordance with the primary aspect of the present invention, a pass-through closure comprises a peripheral rim for defining an opening in a wall with a plurality of generally triangular flaps extending inward and axially, forming a generally conical configuration.

BRIEF DESCRIPTION OF THE DRAWINGS

The above and other objects and advantages of the present invention will become apparent from the following description when read in conjunction with the drawings wherein: FIG. 1 is a perspective view of a preferred embodiment of the closure in accordance with the invention;

FIG. 2 is a top plan view of the embodiment of FIG. 1;

FIG. 3 is a side elevation view with portions cut away to show details; and

FIG. 4 is a partial section view enlarged to show details.

DETAILED DESCRIPTION OF A PREFERRED EMBODIMENT

Referring to FIG. 1 of the drawings, a closure designated generally by the numeral 10 is shown which illustrates the preferred embodiment of the invention.

The closure is a pass-through closure designed to permit the passage of articles principally in one direction only. The closure comprises a generally peripheral frame member 12 which in the illustrated embodiment is of a generally circular configuration surrounding an opening in the neck of a bottle 14. The closure may have any number of configurations or flanges and the like for attachment to a wall or opening of a container as will be subsequentially described.

The peripheral support rim 12 forms an opening and supports a plurality of generally triangular panels 16 which are secured or hinged at the base thereof and extend inward and axially along the axis of the opening, preferably in a direction toward the interior of the container. As can be seen in FIGS. 1, 2 and 3, this forms a conical or funnel like shape or configuration that permits the easy passage of articles in one direction but frustrates or inhibits the passage of articles in the opposite direction. As shown in FIG. 3, articles can easily pass in the direction of the arrow toward what would be the interior of the container of FIG. 1.

Each of the panels 16, which forms the substance of the closure, is preferably formed of a high impact but yieldable, yet somewhat rigid plastic such as polypropylene, polyurethane, polyethylene or the like. Each panel is sufficiently thin and flexible at the juncture 20 with the rim 12 to substantially define a hinge permitting the panel to pivot away from the closed position to permit the passage of articles and the like. Each of the panels is preferably formed with a reinforcing rib 18 which extends from the base to the tip as shown in FIG. 2. Each of the panels is also tapered down to a somewhat rounded point providing a very small opening as opposed to the opening defined by the supporting rim 12. The panels may also be provided with a fairly sharp edge, particularly at the tip. Each of the panels is preferably, as explained, hinged at the base 20 thereof to the peripheral supporting rim 12 and forms a generally triangular configuration extending downward to a somewhat convexly rounded tip 22 as shown in FIG. 2. This construction of the panels forming the closure, as explained above, permits the panels to hinge or swing back from its normally biased closed position to permit the passage of particles therethrough in the one direction.

The closure is primarily designed for disposable containers such as disclosed in our prior patent for disposal of sharps and hazardous objects. The configuration, as illustrated and described, thereby permits the ready passage of articles in one direction through the closure (FIG. 3), yet inhibits the passage in the opposite direction.

The closure assembly is preferably molded or formed of a plastic and may, for example, be injection molded with the arrangement forming a mounting rim or skirt 24 which is adapted to extend down over and attach to a portion of the neck of a container. The skirt and flange of the rim are preferably formed to also form a locking rim 26 which is adapted to cooperate with a V groove 28 on the interior of a cylindrical skirt 30 of a permanent closure 32 such as covered in our prior application Ser. No. 533,608, now U.S. Pat. No. 4,502,606, entitled "Locking Closure For Disposable Containers". The permanent closure 32 is designed to lock in place over the pass-through closure and be essentially non-removable. Thus, when a container is substantially filled, the permanent closure is locked in place and the container disposed of in a suitable fashion. In the illustrated arrangement, the permanent closure 32 is non-removably attached to the rim of the pass-through closure by means of a tethering strap 34 which orients the permanent closure in a direction away from the pass-through closure such that one must consciously manipulate the permanent closure to a 180° orientation before it may be secured in place over the pass-through closure. This prevents the container from being prematurely closed. The permanent closure locks in place as illustrated in FIGS. 3 and 4.

Referring to FIG. 1, the rim 12 may be provided with one or more removal devices 36 and 38 which comprise openings in the rim having sides that are of a width and configuration, such as stepped for example, to form a wrench like device for gripping the hubs of needles for removing them from syringes and the like.

The closure is designed to discourage the unauthorized removal of objects from a container. The closure panels 16 are constructed and arranged so that they form small opening (FIG. 2) and a light force can force them back to form a greater opening for the passage of articles in the one direction (FIG. 3) into the container. Any force in the opposite direction will tend to force the panels inward toward the opening axis and restrict the passage of an article in that direction out of the container. The ends (tips) 22 of the panels will tend to grip an article when it is forced in a direction opposite the arrow (FIG. 3) and the direction the ends 22 are generally pointed.

While we have illustrated and described our invention by means of specific embodiments, it is to be understood that numerous changes and modifications may be made therein without departing from the spirit and scope of the invention as defined in the appended claims.

We claim:

1. A pass-through closure, comprising:
    a circular peripheral supporting rim defining an opening, wherein said rim is substantially flat and circular in configuration and includes a planar area in which is formed a needle hub wrench;
    a plurality of generally triangular shape panels reinforced by rib means to be substantially rigid, said panels being hinged at the base thereof to said rim and normally biased and extending inwardly toward the center and axially of said opening forming a generally conical configuration with the apex of each panel being rounded and terminating proximate the center of said opening for closing said opening; and
    a permanent closure member for selectively engaging said supporting rim for selectively permanently closing said opening.

2. A pass-through closure, comprising:
    a circular peripheral supporting rim defining an opening;
    a plurality of generally triangular shaped panels reinforced by rib means to be substantially rigid, said panels being hinged at the base thereof to said rim and normally biased and extending inwardly toward the center and axially of said opening forming a generally conical configuration with the apex of each panel being rounded and terminating proximate the center of said opening for closing said opening; and
    a permanent closure member for selectively engaging said supporting rim for selectively permanently closing said opening, wherein said permanent closure member is non-removably attached to said supporting rim by a tethering strap.

3. A pass-through closure, comprising:
    a circular peripheral supporting rim having permanent attachment means for permanent attachment to a disposable container and defining an opening;
    a plurality of generally triangular shaped panels including rib means for making the panels substantially rigid, said panels being hinged at the base thereof to said rim and being biased and extending inwardly toward the center and axially of said opening forming a generally conical configuration with the apex of each panel terminating proximate the center of said opening for closing said opening; and
    a permanent closure member for selectively engaging said supporting rim for selectively permanently closing said opening.

4. A pass-through closure according to claim 3 wherein said panels are rounded convexly at the apex thereof.

5. A pass-through closure, comprising:
    a circular peripheral supporting rim defining an opening, wherein said rim is substantially flat and circular in configuration and includes a planar area in which is formed a needle hub wrench;
    a plurality of generally triangular shaped panels reinforced by rib means to be substantially rigid, said panels being hinged at the base thereof to said rim and normally biased and extending inwardly toward the center and axially of said opening forming a generally conical configuration with the apex of each panel being rounded and terminating proximate the center of said opening for closing said opening, wherein said panels are rounded convexly at the apex thereof; and,
    a permanent closure member for selectively engaging said supporting rim for selectively permanently closing said opening.

6. A pass-through closure according to claim 5 wherein said permanent closure member is non-removably attached to said supporting rim by a tethering strap.

7. A one-way pass-through closure, comprising:
    a substantially flat circular peripheral supporting rim defining an opening for a container and including needle hub wrench means formed therein;
    a plurality of panels having a generally triangular shape hingedly secured at the base thereof to said rim, each of said panels extending inwardly toward and axially along the axis of said opening, and said panels together forming a generally conical shaped closure for providing free passage of articles through said closure in one direction and for inhibiting passage of articles through said closure in the other direction; and
    a permanent closure member non-removably attached to said supporting rim by tethering means for selectively engaging said supporting rim for selectively permanently closing said opening.

8. A pass-through closure according to claim 7 wherein said panels are rounded convexly at the apex thereof.

* * * * *